United States Patent [19]

Winston

[11] Patent Number: 5,464,805
[45] Date of Patent: * Nov. 7, 1995

[54] METHOD OF CONTROLLING MILDEW IN CULTIVATED PLANTS

[75] Inventor: Anthony E. Winston, East Brunswick, N.J.

[73] Assignee: Church & Dwight Co., Inc., Princeton, N.J.

[ * ] Notice: The portion of the term of this patent subsequent to Jun. 13, 2012, has been disclaimed.

[21] Appl. No.: 408,787

[22] Filed: Mar. 23, 1995

Related U.S. Application Data

[60] Division of Ser. No. 149,310, Nov. 9, 1993, which is a continuation-in-part of Ser. No. 984,532, Dec. 2, 1992, abandoned.

[51] Int. Cl.$^6$ .......... A01N 37/02; A01N 59/00; C05G 3/02; C05G 3/06
[52] U.S. Cl. .......... 504/101; 424/715; 424/716; 424/717; 514/557; 514/558; 514/560; 514/709; 514/772; 514/772.1; 514/772.3; 514/772.6; 514/773; 514/775; 514/777; 514/778; 514/779; 514/780; 514/781; 514/782; 514/783; 514/784; 71/DIG. 1
[58] Field of Search .......... 504/101; 424/715, 424/716, 717; 514/557, 558, 560, 709, 772, 772.1, 772.3, 772.6, 773, 775, 777, 778, 779, 780, 781, 782, 783, 784; 71/DIG. 1

[56] References Cited

U.S. PATENT DOCUMENTS

| | | | |
|---|---|---|---|
| 1,560,558 | 11/1925 | Fulton et al. | 424/715 |
| 4,599,233 | 7/1986 | Misato et al. | 424/717 |
| 4,692,466 | 9/1987 | Yoshimoto et al. | 514/604 |
| 5,030,658 | 7/1991 | Salloum et al. | 514/560 |
| 5,093,124 | 3/1992 | Kulenkampff | 424/406 |

FOREIGN PATENT DOCUMENTS

| | | |
|---|---|---|
| 53-96319 | 8/1978 | Japan . |
| 60-153785 | 8/1985 | Japan . |

OTHER PUBLICATIONS

Farm Chemicals Handbook '87, Meister Publishing Co., Ohio, 1987, pp. C230 and C236.

*Primary Examiner*—Allen J. Robinson
*Assistant Examiner*—John D. Pak
*Attorney, Agent, or Firm*—Charles B. Barris

[57] ABSTRACT

The present invention provides a method for controlling mildew in cultivated crops. The aqueous fungicide formulation which is applied to pre-harvest and post-harvest crops contains ingredients which are biocompatible for purposes of agricultural and horticultural applications. Illustrative of a formulation which is harmless to animals and humans is an aqueous solution having a content of potassium bicarbonate, potassium carbonate, potassium oleate and xanthan gum. The combination of potassium oleate and xanthan gum functions as an effective spreader-sticker medium for forming a solid coating on plant surfaces. The solid coating exhibits both immediate and long duration fungicidal activities.

7 Claims, No Drawings

METHOD OF CONTROLLING MILDEW IN CULTIVATED PLANTS

CROSS-REFERENCE TO RELATED PATENT APPLICATION

This application is a division of patent application Ser. No. 08/149,310, filed Nov. 9, 1993, which is a continuation-in-part of patent application Ser. No. 07/984,532, filed Dec. 2, 1992, now abandoned.

BACKGROUND OF THE INVENTION

The control of phytopathogenic fungi is of great economic importance since fungal growth on plants or on parts of plants inhibits production of foliage, fruit or seed, and the overall quality of a cultivated crop. About 25 percent of all fungal diseases in agriculture and horticulture are caused by powdery mildew phytopathogens.

Because of the vast economic ramifications of fungal propagation in agricultural and horticultural cultivations, a broad spectrum of fungicidal and fungistatic products have been developed for general and specific applications.

Of particular interest with respect to the present invention embodiments are fungicide compositions which contain an inorganic bicarbonate or carbonate compound. It is known that bicarbonate and carbonate compounds exhibit fungicidal properties for agricultural purposes.

Phytopathology, 48, 169 (1931) by R. H. Marloth describes studies involving the physiology of fungi. The reference reports studies which demonstrate that sodium and potassium bicarbonate and carbonate salts are toxic to fungi such as *Penicillum italicum* and *Penicillum digitalum*.

U.S. Pat. No. 1,560,558 discloses the use of salts such as lithium carbonate, sodium carbonate, sodium bicarbonate, potassium bicarbonate, potassium carbonate and ammonium bicarbonate as fungicide ingredients.

U.S. Pat. No. 4,599,233 describes a fungicide composition which consists of sodium bicarbonate in combination with a surface active food emulsifier such as sorbitan monostearate.

Japanese patent 53118523 describes the combination of sodium bicarbonate and lecithin as an active agent for the control of agricultural and fruit storage fungus diseases.

Japanese patent 56043207 describes a biocidal composition containing sodium bicarbonate and a polyglycerol fatty acid ester. The biocide controls *Penicillum digitatum* on oranges, *Sphaerotheca fuligenea* on cucumbers, *Piricularia oryzae* on rice, and mosaic virus on tomatoes.

Japanese patent 60097909 describes a soil fungicide prepared by admixing slaked lime with sodium bicarbonate, potassium bicarbonate, boric acid and phenolphthalein.

German patent DE 2927994 describes a fungicide which consists of sodium bicarbonate incorporated into a food-compatible surfactant such as saccharose laurate.

Japanese patent 57062208 describes horticultural fungicides in which the addition of sodium bicarbonate to polyoxin or thiophanatemethyl increases the fungicidal activity of the organic biocide against *Botrytis cinerea* on cucumbers.

Japanese patent 58023609 describes an agricultural fungicide composed of a mixture of sodium bicarbonate or potassium bicarbonate with cupric hydroxide, basic copper carbonate or basic copper sulfate. The combination of ingredients exhibits a synergistic fungicidal effect against cucumber early blight, tomato wilt, rice sheath blight, rice blast and citrus canker.

There remains a continuing need for improved methods for providing preventive and curative fungicidal activity for the protection of cultivated plants with a minimum of phytotoxic side effects, and with safety for animals and humans.

Accordingly, it is an object of this invention to provide a method of controlling mildew diseases in cultivated plants.

It is another object of this invention to provide a method for controlling mildew in agricultural and horticultural plants with an aqueous fungicidal formulation having a content of ingredients which are harmless to animals and humans.

It is another object of this invention to provide a method of controlling powdery mildew and downy mildew in pre-harvest and post-harvest crops with an aqueous formulation which forms a solid coating on plant matter exhibiting fungicidal activity of sustained duration.

Other objects and advantages of the present invention shall become apparent from the accompanying description and examples.

DESCRIPTION OF THE INVENTION

One or more objects of the present invention are accomplished by the provision of a method for controlling mildew disease in cultivated plants which comprises contacting the plant matter with a fungicidally effective application of an aqueous formulation which has a content comprising (1) about 0.1–2 weight percent of an ingredient selected from alkali metal and ammonium bicarbonates; (2) about 0.05–1.5 weight percent of a basic ingredient selected from alkali metal and ammonium carbonates; (3) about 0.05–2 weight percent of a surfactant ingredient selected from alkali metal and ammonium $C_8$–$C_{22}$ aliphatic-containing carboxylate, sulfonate, sulfate and phosphate salts; and (4) about 0.01–0.5 weight percent of a water-soluble pseudoplastic thickener ingredient; based on the formulation weight.

An invention aqueous formulation can be prepared by pre-blending the solid ingredients, and then dispersing the blended admixture in an aqueous medium to a selected concentration of bicarbonate ingredient.

An invention aqueous formulation can be prepared as a concentrated medium which is diluted further before usage, or the dilute aqueous formulation can be prepared directly by adding the individual ingredients or a pre-blend of ingredients to an aqueous medium.

An invention dilute aqueous fungicidal solution is in a ready-to-use form which can be applied directly to the foliage of plants, bushes and trees, such as by electrodynamic spraying techniques. A solid film-like coating forms on the plant matter surfaces after the aqueous medium has evaporated.

The bicarbonate salt ingredient of an invention fungicide formulation is sodium bicarbonate, potassium bicarbonate or ammonium bicarbonate, or any mixture thereof.

Illustrative of a bicarbonate salt ingredient in a formulation are sodium, potassium or ammonium bicarbonate; or mixtures such as sodium bicarbonate and potassium bicarbonate; sodium bicarbonate and ammonium bicarbonate; potassium bicarbonate and ammonium bicarbonate; sodium bicarbonate, potassium bicarbonate and ammonium bicarbonate; and the like.

The basic salt ingredient of an invention fungicide formulation is sodium carbonate, potassium carbonate, ammonium carbonate or lithium carbonate, or any mixture thereof.

Multiple inorganic salt compounds can be utilized in a broad range of molar quantities relative to each other. In one aspect the molar quantity of a carbonate salt compound is determined by pH control considerations when aqueous formulations are prepared. The content of a carbonate salt compound can be varied to control the pH of an aqueous fungicide formulation at a desired level in the range of about 7.5–11. An aqueous fungicide formulation of the present invention tends to have a higher fungicidal activity at higher pH values.

The inclusion of a carbonate salt ingredient in an aqueous fungicide formulation is an important feature of the present invention means of controlling mildew disease in agricultural and horticultural plant life. In addition to providing alkaline pH control, the carbonate salt potentiates the fungicidal activity of the bicarbonate salt ingredient. Further, under ambient atmospheric conditions, the carbonate salt in the solid coating on plant matter surfaces reacts with carbon dioxide and moisture to form bicarbonate salt in situ over a prolonged duration. An invention aqueous fungicide formulation exhibits both immediate fungicidal activity after application, and long duration fungicidal activity under ambient conditions.

The surfactant ingredient of an invention fungicide formulation is an anionic surface active derivative selected from alkali metal and ammonium $C_8$–$C_{22}$ aliphatic-containing carboxylate, sulfonate, sulfate and phosphate salts. These anionic surfactants provide superior dispersant activity when an invention aqueous formulation is prepared.

An invention aqueous formulation is in the form of a stable aqueous dispersion which exhibits excellent spreader-sticker and film-forming properties when applied to plant foliage.

Surfactants which provide suitable dispersant properties are anionic compounds such as alkyl sulfates and alkyl ether sulfates having 8–20 carbon atoms in the alkyl group. The ether sulfates can contain about 1–10 oxyethylene groups in the molecule. The sulfate surfactants can be in the form of sodium, potassium, ammonium or lower alkanolamine salts.

Other suitable anionic surfactants include sodium and potassium alkylbenzenesulfonates, in which the alkyl group contains about 9–15 carbon atoms; sodium alkyl glycerol ether sulfonates; sodium coconut oil fatty acid monoglyceride sulfates and sulfonates; sodium salts of sulfuric acid esters of oxyethylated fatty alcohols; sodium sulfosuccinate esters; condensation products of fatty acids with sarcosine; monoester or diester phosphates of $C_{10}$–$C_{18}$ fatty alcohols in the form of sodium, potassium or ammonium salts (e.g., Gafac PE-510, GAF Corporation); and the like. Anionic surfactants are described in references such as U.S. Pat. Nos. 4,528,039 and 5,037,818, incorporated herein by reference.

Other suitable anionic surfactants are $C_8$–$C_{22}$ fatty acid salts selected from alkali metal and ammonium salts of natural straight chain and synthetic branched chain fatty acids, which have a saturated or unsaturated structure. Illustrative of natural fatty acids are caprylic acid, pelargonic acid, capric acid, lauric acid, myristic acid, palmitic acid, stearic acid, oleic acid, linoleic acid, arachidic acid, behenic acid, cetoleic acid, and the like.

A $C_8$–$C_{22}$ fatty acid salt ingredient can consist of two or more saturated or unsaturated carboxylic acids such as those derived from beef and mutton tallow, lard, cottonseed oil, palm oil, and the like.

The thickener ingredient of an invention fungicide formulation is selected from water-soluble organic polymers which exhibit pseudoplastic rheological properties in an aqueous medium.

The term "water-soluble" as employed herein refers to a thickener ingredient which has a solubility of at least about one gram per 100 grams of water at 25° C.

The term "pseudoplastic" as employed herein refers to the rheological behavior of an aqueous solution containing a dissolved thickener ingredient, in which the apparent viscosity of the aqueous solution decreases with increasing shear rate.

Illustrative of water-soluble polymers which exhibit pseudoplastic properties in an aqueous medium are gum arabic, gum karaya, gum tragacanth, guar gum, locust bean gum, xanthan gum, carrageenan, alginate salt, casein, dextran, pectin, agar, 2-hydroxyethyl starch, 2-aminoethyl starch, 2-hydroxyethyl cellulose, methyl cellulose, carboxymethyl cellulose salt, cellulose sulfate salt, polyacrylamide, methyl vinyl ether/maleic anhydride copolymer, styrene/maleic anhydride copolymer, ethylene/maleic anhydride copolymer, the corresponding alkali metal salts of the maleic anhydride copolymers, alkali metal salts of poly(meth)acrylate, and the like.

Many of the water-soluble polymers are large volume commercial products. Sodium carboxymethyl cellulose (CMC) is available in powder or granular form having a particle size of 50–200 microns. CMC is available in a degree of substitution (DS) range of 0.38–1.4.

One type of preferred aqueous formulation in accordance with the present invention is one containing alkali metal or ammonium bicarbonate, alkali metal or ammonium carbonate, alkali metal or ammonium $C_8$–$C_{22}$ fatty acid salt, and a hydrocolloid gum.

The ingredients in an invention fungicide formulation can be selected to include nitrogen, phosphorus and potassium elements in a ratio that qualifies the composition to function as a fertilizer in addition to its function as a fungicide, when applied to cultivated crops. When an aqueous solution containing fertilizer elements is sprayed on plant foliage, there is direct absorption of the fertilizer elements into the leaves.

In another embodiment this invention provides a method for controlling mildew disease in cultivated plants which comprises contacting the plant matter with a fungicidally effective application of an aqueous formulation which has a content comprising (1) about 0.1–2 weight percent of an ingredient selected from alkali metal and ammonium bicarbonates; (2) about 0.05–1.5 weight percent of a basic ingredient selected from alkali metal and ammonium carbonates; (3) about 0.05–2 weight percent of a surfactant ingredient selected from alkali metal and ammonium $C_8$–$C_{22}$ aliphatic-containing carboxylate, sulfonate, sulfate and phosphate salts; (4) about 0.01–0.5 weight percent of a water-soluble pseudoplastic thickener ingredient; and (5) about 0.1–2 weight percent of an ingredient selected from phosphorus-containing fertilizer compounds; based on the formulation weight; wherein the ingredients have a formulated ratio of nitrogen, phosphorus and potassium elements.

Besides nitrogen, phosphorus and potassium, an invention fungicide fertilizer composition can contain trace elements, and other essential elements as exemplified by sulfur as contained in a compound such as sodium bisulfite or thiourea.

An invention fungicide formulation can include one or more other biologically active ingredients, such as those which exhibit herbicidal, insecticidal or plant growth regulating activity.

A fungicide formulation of the present invention has a novel combination of properties for the practice of pesticide control in agricultural and horticultural applications.

The bicarbonate and carbonate ingredients exhibit fungicidal properties, and the efficacy of any additionally included organic pesticide ingredient usually is enhanced by the presence of the combination of bicarbonate and carbonate salts. A lesser quantity of optional pesticide ingredient can be employed to achieve a desired degree of pest control.

A present invention aqueous fungicide medium can be formulated to exhibit no phytotoxicity, or to minimize the toxic effects of salt stress on plants by the bicarbonate and carbonate ingredients.

A present invention fungicide formulation provides particular advantage for the control of infectious phytopathogenic fungi which thrive under acidic soil conditions.

All of the fungicide formulation ingredients are biocompatible when the composition is applied in an agricultural environment. The bicarbonate, carbonate, surfactant and thickener ingredients are all harmless to animals and humans.

A significant feature of a present invention fungicide formulation is the presence of surfactant and thickener ingredients, which function as a spreader-sticker medium when the fungicide formulation is applied to plant foliage as an aqueous solution. An applied aqueous solution forms an adherent coating of ingredients on plant foliage or fruit. The surfactant ingredient aids in spreading and sticking the fungicide formulation ingredients to the foliage or fruit to which it is applied. The pseudoplastic thickener ingredient increases the amount of aqueous fungicide composition which adheres to the plant matter surfaces because of its static high apparent viscosity. During a spraying procedure, the pseudoplastic thickener ingredient contributes a low mobile viscosity to the spray solution, which facilitates the spraying action. After spraying, the resultant solid coating resists drifting under wind conditions, and exhibits humectant properties in addition to enhanced fungicidal activity.

Another important advantage of an invention fungicide formulation derives from the water-solubility of the contained ingredients. The solid coating of an invention fungicide formulation on plant matter surfaces can be removed readily by water-washing. Conventional fungicide formulations which contain a petroleum-based spreader-sticker ingredient leave an oily residue on treated plant foliage or fruit which is difficult to remove.

A present invention fungicide formulation is adapted for application to harvested crops to prevent or eradicate mildew disease, or to inhibit re-infection by phytopathogenic mildew fungi.

A present invention fungicide formulation has particular advantage for the control of powdery mildew and downy mildew in crops such as ornamental stock, bedding plants, turf, cereals, vegetables, fruits, forest trees, and the like.

Illustrative of particular crops are pre-harvest and post-harvest stages of grape, apple, pear, peaches, strawberry, raspberry, cucumber, rose, and the like.

A present invention fungicide formulation is biocidally effective against powdery mildew species which include *Erysiphe asperifolium, Erysiphe betae, Erysiphe cichoracearum, Erysiphe cruciferarum, Erysiphe galeopsidis, Erysiphe graminis, Erysiphe pisi, Erysiphe polygoni, Erysiphe ranunculi, Erysiphe trifolii, Erysiphe verbasci, Microsphaera alphitoides, Oidium euonymi-japonicae, Oidium hortensiae, Podosphaera leucotricha, Podosphaera tridactyla, Sphaerotheca alchemillae, Sphaerotheca fuliginea, Sphaerotheca maculans, Sphaerotheca pannosa, Uncinula bicornis* and *Uncinula necator.*

A present invention fungicide formulation also is biocidally effective against downy mildew species which include *Peronospora antirrhini, Peronospora arborescens, Peronospora destructor, Peronospora farinosa, Peronospora ficariae, Peronospora galligena, Peronospora grisea, Peronospora lamii, Peronospora parasitica, Peronospora sparsa, Peronospora trifoliorum, Peronospora viciae, Pseudoperonospora humuli,* and *Plasmopara vitacola.*

The following examples are further illustrative of the present invention. The components and specific ingredients are presented as being typical, and various modifications can be derived in view of the foregoing disclosure within the scope of the invention.

EXAMPLE I

This Example illustrates the preparation of a fungicide powder concentrate in accordance with the present invention.

A blend of the following ingredients is prepared:

|  | Parts |
| --- | --- |
| sodium bicarbonate | 40 |
| potassium bicarbonate | 20 |
| potassium carbonate | 5 |
| potassium oleate | 25 |
| xanthan gum | 10 |

The formulated concentrated powder is diluted with water by the dispersion of 1 part of the powder blend into 100 parts of water. The resulting solution is sprayed onto strawberry plants, where it forms an adherent solid coating on the foliage surfaces of the plants.

EXAMPLE II

This Example illustrates the preparation of a fungicidal formulation in accordance with the present invention.

|  | Parts |
| --- | --- |
| potassium bicarbonate | 50 |
| sodium carbonate | 5 |
| potassium oleate | 15 |
| sodium stearate | 15 |
| sodium carboxymethyl-cellulose[1] | 15 |
| water | 50 |

[1]Aldrich Chemical Co., CMC of 3000–6000 centipoises, intrinsic viscosity of 2% aqueous solution at 25° C.

The solid ingredients are blended, and the blend is suspended in water to form an aqueous emulsion.

The emulsion formulation is diluted with water to 0.2% by weight of bicarbonate ingredient. The diluted formulation is tested as a fungicide medium against plant foliage infected with *Erysiphe cichoracearum* powdery mildew. The fungicidal medium is 100% effective in mildew eradication, and prevents re-infection in a field planting of cantaloupe when sprayed four times at ten day intervals.

EXAMPLE III

This Example illustrates the preparation of a concentrated aqueous fungicidal formulation.

|  | Parts |
| --- | --- |
| potassium bicarbonate | 20.00 |
| potassium carbonate | 4.00 |
| potassium oleate | 15.00 |
| potassium octanoate | 5.00 |
| xanthan gum | 2.00 |
| butylated hydroxytoluene (BHT) | 0.02 |
| water | 57.98 |

Potassium octanoate is included in the formulation to serve as a hydrotrope to prevent precipitation of potassium oleate from solution.

The aqueous concentrate is prepared by dissolving the potassium bicarbonate and potassium carbonate in the water, and then with stirring adding the other ingredients.

The prepared concentrated aqueous formulation is diluted 1 part to 40 parts of water. The diluted formulation is effective for prevention of powdery mildew and downy diseases on cultivated plants. The formulation controls *Sphaerotheca pannosa* powdery mildew on roses, *Plasmopara vitacola* downy mildew and *Uncinula necator* powdery mildew on grapevines, and *Sphaerotheca fuligenea* powdery mildew on cucurbits.

Superior fungicidal results are obtained when the active ingredients are potassium bicarbonate, potassium carbonate, potassium oleate and xanthan gum.

EXAMPLE IV

This Example illustrates the preparation of a partially diluted aqueous fungicidal formulation.

|  | Parts |
| --- | --- |
| potassium bicarbonate | 5.00 |
| potassium carbonate | 1.00 |
| potassium oleate | 5.00 |
| butylated hydroxytoluene (BHT) | 0.02 |
| potassium polyacrylate[1] | 2.00 |
| water | 86.98 |

[1]polyacrylic acid K salt; M.W. of 200,000.

The potassium polyacrylate is dissolved in the water. The potassium bicarbonate and carbonate are added to the aqueous solution, followed by the addition of potassium oleate and BHT.

The aqueous solution is diluted with 9 parts of water per part of solution. The diluted solution is effective for controlling powdery mildew, downy mildew and *Botrytis cinerea* fungal diseases when applied to harvested vegetables and fruits.

EXAMPLE V

This Example illustrates the preparation of a dilute aqueous fungicidal formulation which is ready-to-use in agricultural applications.

|  | Parts |
| --- | --- |
| sodium bicarbonate | 0.50 |
| sodium carbonate | 0.05 |
| potassium oleate | 0.20 |
| butylated hydroxytoluene (BHT) | 0.02 |
| sodium alginate | 0.48 |
| water | 98.00 |

The sodium alginate is dissolved in the water, followed by the successive addition of sodium bicarbonate, sodium carbonate, potassium oleate and BHT.

The dilute formulation is effective for control of *Erysiphe graminis* powdery mildew disease when sprayed on test plots of cereal and fodder crops.

EXAMPLE VI

This Example illustrates the preparation of an aqueous fungicidal formulation which contains a mixture of bicarbonate compounds.

|  | Parts |
| --- | --- |
| potassium bicarbonate | 6 |
| sodium bicarbonate | 6 |
| ammonium carbonate | 6 |
| ammonium palmitate | 12 |
| xanthan gum | 2 |
| water | 68 |

The ingredients are added to the water to form an aqueous formulation in the manner previously described.

The formulation in diluted form is more effective than a comparative formulation containing a single bicarbonate compound, for controlling a broad range of foliar and soil-born resistant fungi.

The ammonium carbonate ingredient of the solid coating which forms on plant foliage provides in situ formation of ammonium bicarbonate, and the solid coating exhibits a prolonged duration of fungicidal activity.

EXAMPLE VII

This Example illustrates the preparation of a fungicide-fertilizer composition for application to plant foliage and soil.

|  | Parts |
| --- | --- |
| potassium bicarbonate | 10 |
| ammonium carbonate | 7 |
| potassium oleate | 5 |
| potassium octanoate | 3 |
| carrageenan | 2 |
| urea | 5 |
| dipotassium orthophosphate | 2 |
| water | 66 |

The ingredients are dispersed in the water to form a concentrated solution. The solution is diluted 1 part solution to 20 parts water before use.

A container of the solution is connected to agricultural sprayer equipment, and sprayed through a hollow cone spray nozzle at a pressure of 250 psi. The spray droplet size is 100–150 microns. A selected plot of oak saplings is sprayed with the solution at 20 day intervals during the spring-summer growing season, and is effective for preventing powdery mildew fungal infection of the trees, and for promoting healthy growth. An untreated plot of oak saplings shows evidence of *Microphaera alphitoides* infection damage.

EXAMPLE VIII

This Example illustrates the effectiveness of an invention fungicidal formulation containing bicarbonate/carbonate ingredients for the control of powdery mildew on rose plants.

Greenhouse cultivated Sonia rose plants infected with powdery mildew (*Sphaerotheca pannosa* var. *rosae*) are sprayed weekly with the following formulations:

|  | Control A | I |
|---|---|---|
| Water | 71.62 | 66.48 |
| Polyvinylpyrrolidone | 0.00 | 5.00 |
| Xanthan gum | 0.00 | 0.50 |
| Potassium bicarbonate | 20.00 | 10.90 |
| Potassium carbonate | 0.00 | 4.10 |
| Sodium Bicarbonate | 0.00 | 5.00 |
| BHT | 0.00 | 0.02 |
| Potassium oleate | 4.57 | 8.00 |
| Potassium caprylate | 3.81 | 0.00 |

The results are as follows:

| | AVERAGE DISEASE RATING* | | | |
|---|---|---|---|---|
| | Successive Weekly Treatments | | | |
| No treatment | 3.36 | 3.81 | 3.94 | 4.55 |
| Water Control | 3.74 | 2.91 | 4.37 | 4.40 |
| Control A | 2.29 | 1.36 | 1.31 | 1.62 |
| Example I | 1.31 | 0.35 | 0.20 | 0.49 |

*disease rating: 0 = no mildew, 1 = 10% coverage, 2 = 25% coverage, 3 = 50% coverage, 4 = 75% coverage, 5 = 95–100% coverage.

Similar fungicidal results are obtained with Royalty and Mary Devor rose varieties.

What is claimed is:

1. A method for controlling mildew disease in cultivated plants which comprises contacting the plant matter with a fungicidally effective application of an aqueous formulation which has a content comprising (1) about 0.1–2 weight percent of an ingredient selected from the group consisting of alkali metal and ammonium bicarbonates; (2) about 0.05–1.5 weight percent of a basic ingredient selected from the group consisting of alkali metal and ammonium carbonates; (3) about 0.05–2 weight percent of a surfactant ingredient selected from the group consisting of alkali metal and ammonium $C_8$–$C_{22}$ aliphatic-containing carboxylate, sulfonate, sulfate and phosphate salts; (4) about 0.01–0.5 weight percent of a water-soluble pseudoplastic thickener ingredient; and (5) about 0.1–2 weight percent of an ingredient selected from the group consisting of phosphorus-containing fertilizer compounds; based on the formulation weight; wherein the ingredients have a formulated fertilizer-effective amount and ratio of nitrogen, phosphorus and potassium elements; and. wherein the pH of the formulation is in the range between about 7.5–10.5.

2. A method in accordance with claim 1 wherein the basic ingredient is sodium carbonate, potassium carbonate, ammonium carbonate or lithium carbonate, or any mixture thereof.

3. A method in accordance with claim 1 wherein the thickener ingredient comprises a hydrocolloid gum.

4. A method in accordance with claim 1 wherein the thickener ingredient comprises a cellulosic derivative.

5. A method in accordance with claim 1 wherein the thickener ingredient comprises a starch derivative.

6. A method in accordance with claim 1 wherein the thickener ingredient comprises xanthan gum, guar gum or carrageenan gum.

7. A method in accordance with claim 1 wherein the aqueous formulation additionally contains sulfur as an essential fertilizer element.

* * * * *